(12) United States Patent
Toll et al.

(10) Patent No.: US 10,907,303 B2
(45) Date of Patent: Feb. 2, 2021

(54) BIOMASS, THERMAL PRESSURE HYDROLYSIS AND ANAEROBIC DIGESTION

(71) Applicant: THERMO PRESSURE TECHNOLOGIES LIMITED, Dublin (IE)

(72) Inventors: Ian Cecil Toll, Dorset (GB); Christian Andrew Ian Toll, Dorset (GB); Nigel Anthony Bailey, Dorset (GB); Zhengjian Wang, Dorset (GB); Andrew Walsh, County Cork (IE)

(73) Assignee: THERMO PRESSURE TECHNOLOGIES LIMITED, Dublin (IE)

( * ) Notice: Subject to any disclaimer, the term of this patent is extended or adjusted under 35 U.S.C. 154(b) by 259 days.

(21) Appl. No.: 16/064,915

(22) PCT Filed: Dec. 19, 2016

(86) PCT No.: PCT/GB2016/053987
§ 371 (c)(1),
(2) Date: Jun. 21, 2018

(87) PCT Pub. No.: WO2017/109468
PCT Pub. Date: Jun. 29, 2017

(65) Prior Publication Data
US 2020/0157739 A1    May 21, 2020

(30) Foreign Application Priority Data
Dec. 23, 2015   (GB) .................................. 1522750.7

(51) Int. Cl.
*D21C 1/02*       (2006.01)
*C12P 5/02*       (2006.01)
(Continued)

(52) U.S. Cl.
CPC ................ *D21C 1/02* (2013.01); *C12P 5/023* (2013.01); *D21B 1/36* (2013.01); *D21C 3/26* (2013.01);
(Continued)

(58) Field of Classification Search
CPC .... D21C 1/02; D21C 3/26; D21C 7/02; C12P 2201/00; C12P 5/023
See application file for complete search history.

(56) References Cited

U.S. PATENT DOCUMENTS

| 8,470,177 | B2 * | 6/2013 | Dvorak | ................... | C02F 3/286 |
| | | | | | 210/259 |
| 9,056,294 | B2 * | 6/2015 | Fink | ........................ | B01J 8/002 |

(Continued)

FOREIGN PATENT DOCUMENTS

| WO | WO2006042551 A1 | 4/2006 |
| WO | WO2007138534 A1 | 12/2007 |

(Continued)

OTHER PUBLICATIONS

Intellectual Property Office of the United Kingdom, Combined Search and Examination Report under Sections 17 and 18(3) for Application No. GB1522750.7 dated Apr. 27, 2016.

(Continued)

*Primary Examiner* — Nam X Nguyen
*Assistant Examiner* — Julia L. Wun
(74) *Attorney, Agent, or Firm* — Parsons Behle & Latimer (57) ABSTRACT

A process is provided for preparing a low density, fibrous primary lignocellulose biomass, particularly straw for anaerobic digestion at large scale, i.e. >2 $MW_{th}$, which comprises a step that greatly increasing the density of the straw through size reduction, moisture adjustment and compression ahead of loading and subsequent agitation of the (Continued)

resultant biomass in a pressure vessel through an atmosphere of saturated steam providing heat for thermal-pressure hydrolysis and recovering treated biomass from the vessel. The primary lignocellulose biomass may be prepared in admixture with secondary biomass which may be manure-based. There is also provided a feedstock for anaerobic digestion comprising a fibrous primary lignocellulose biomass in a finely divided state, a secondary biomass providing anaerobically digestible nitrogen and aqueous liquid, the primary biomass having a disrupted cellular structure such that its inherent buoyancy in aqueous liquid is lost and digestible carbon is released and the mixture being in the form of an aqueous slurry in a sterilized state. The feedstock after thermal pressure hydrolysis may be anaerobically digested e.g. by wet mesophilic anaerobic digestion to achieve a high unit throughput and biomethane output thus allowing the deployment of the system at large scale within the anaerobic digestion industry.

13 Claims, 6 Drawing Sheets (51) Int. Cl.
*D21C 3/26* (2006.01)
*D21C 7/02* (2006.01)
*D21C 11/00* (2006.01)
*D21B 1/36* (2006.01)

(52) U.S. Cl.
CPC ............ *D21C 7/02* (2013.01); *D21C 11/0007* (2013.01); *C12P 2201/00* (2013.01)

(56) References Cited

U.S. PATENT DOCUMENTS

| | | |
|---|---|---|
| 2009/0221814 A1 | 9/2009 | Pschorn et al. |
| 2011/0081689 A1* | 4/2011 | Flanegan ................. D21C 1/04 |
| | | 435/105 |
| 2012/0282466 A1 | 11/2012 | Iyer et al. |
| 2013/0206345 A1 | 8/2013 | Dauser |

FOREIGN PATENT DOCUMENTS

| | | |
|---|---|---|
| WO | WO2008073186 A2 | 6/2008 |
| WO | WO2012172329 A2 | 12/2012 |
| WO | WO2013082616 A2 | 6/2013 |

OTHER PUBLICATIONS

European Patent Office, International Search Report for PCT Application No. PCT/GB2016/05397 dated Apr. 10, 2017.

* cited by examiner

Fig. 1. Proportion of GB straw production by crop type (2007)

Fig. 5. Methane yield using TPH pre-treated barley straw and barley straw subjected to milling/shredding only.

Fig. 6. Comparison of specific biogas potential between blended cattle manure and barley straw subjected to TPH and shredding only.

Fig. 7. Specific methane potential of TPH treated and un-TPH untreated mixed straw and manure Fig. 8. Methane production per tonne of material processed (TPH treated barley straw mixed with cattle manure compared with a mixture subjected to shredding only.

BIOMASS, THERMAL PRESSURE HYDROLYSIS AND ANAEROBIC DIGESTION

CROSS-REFERENCE TO RELATED APPLICATIONS

This application is the National Stage of International Application No. PCT/GB2016/053987 filed Dec. 19, 2016 which claims priority under 35 U.S.C. § 119(b) from Great Britain Patent Application No. 1522750.7 filed Dec. 23, 2015 the entire contents are hereby incorporated by reference in their entirety.

FIELD OF THE INVENTION

The present invention relates to the preparation a fibrous primary lignocellulose biomass for anaerobic digestion, to the prepared biomass and to a process of anaerobic digestion using the biomass so prepared.

BACKGROUND OF THE INVENTION

Figure 1:
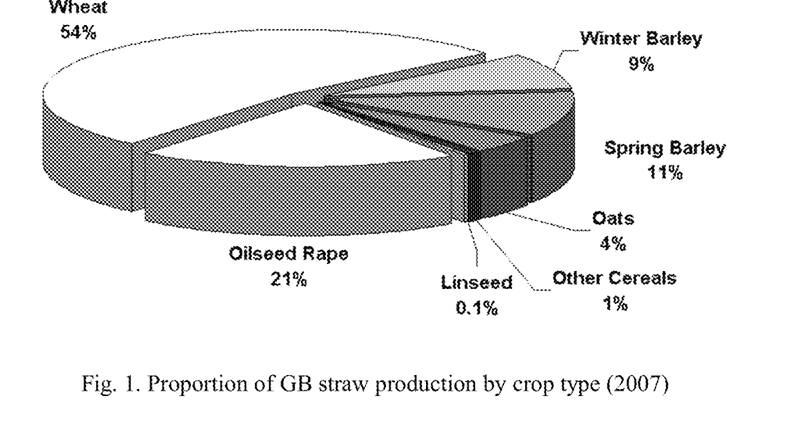
FIG. 1 is a pie-chart showing the proportion of GB straw production by crop type.

Straw is an agricultural residue, being the dry stalks of cereal plants after grain and chaff have been removed. It represents up to half the yield of cereal crops such as barley, oats, rape, rice, rye and wheat. Total straw production of straw in the UK is of the order of 12 million tonnes per annum (Copeland & Turley, National and regional supply/demand balance for agricultural straw in Great Britain, Report prepared for The National Non-Food Crops Centre, November 2008). The approximate proportions of production is illustrated in FIG. 1. Once gathered, straw is usually stored in bales and is typically used as animal bedding or as a roughage component of the diet of cattle or horses. The amounts used for bedding and fodder is estimated at approximately 50% of the straw arising with the remainder being seen as surplus that is often just ploughed back into the ground. The geographic variability in this surplus is described by Copeland and Turley (above).

The possibility of utilizing straw as a biomass source for sustainable energy production was initially deemed to be problematic as straw was initially viewed as an energy crop, i.e. a "co-product" of grain production as opposed to a by-product or residue. This meant that carbon emissions associated with the growing of grain allied to transport costs were considered in relation to the sustainability of the use of straw in energy production. This is described by Bates et al. (2009) wherein the carbon emissions of straw burning power stations were shown to be similar to fossil gas fired stations. Since then however, this position has been reconsidered in the UK in particular and it is now deemed that straw is a residue or waste and not a co-product (OFGEM, 2015) wherein it is deemed that straw is indeed a by-product/waste product of grain production, i.e. it is not the intended primary product when land is used for grain production. Accordingly, three large scale straw burning biomass energy plants have been constructed to target these surpluses in the UK to date. However, at a combined capacity of 500,000 tonnes per annum, this only represents 8% of this surplus. Straw burning as process of deriving energy from straw is therefore limited to those areas where there are significant surpluses allied to the requirement to transport the straw over long distances that could still impact on the sustainability of these large scale plants.

Anaerobic digestion (AD) is in theory another option for the production of renewable energy from straw. However, this has not been attempted at any scale wherein scale is defined as being plants with an output of $>2$ MW$_{th}$/h. There are a number of reasons for this. As straw is very dry ($>85\%$ TS) it is not typically deemed to be a suitable substrate for AD where silage, manure, organic sludge and food waste are typically used, i.e. materials with TS of 5-35%. Furthermore, straw is slow to absorb water due to its waxy exterior thus resists bio-degradation. Straw also has a very low bulk density. Specifically, straw has a loose bulk density of $<50$ kg/m$^3$. Even when chopped, straw remains typically $<100$ kg/m$^3$. This contrasts with conventional AD input substrates such as maize/grass silage that is typically $>400$ kg/m$^3$ and food waste and sludge that is typically $>700$ kg/m$^3$. Such low material density associated with the low biodegradability of such lignocellulose substrates makes the material difficult to handle mechanically and to incorporate into a blend ahead of conventional AD conducted in conventional wet AD systems, i.e. continuously stirred reactors (CSRs). Accordingly on a volume basis such substrates are considered to have a very low energy density compared with conventional feedstocks. Where straw or other such low density lignocellulose substrates is chopped and mixed with other more pumpable substrates, the straw remains buoyant and consequently this can also cause significant mechanical issues in conventional CSRs. Floating layers inevitably develop that can lead to crusts on the surface that can ultimately lead of process failure where such lignocellulose substrates are used in significant quantities. Where it is possible to incorporate straw into a digestion mix (albeit sparingly) the digestible carbon within the straw is also poorly accessible to digestion bacteria due to the hard waxy lignocellulose structural cellular sheath that protects the plant cells. This generally leads to relatively poor biogas yields compared with conventional substrates.

For the above reasons straw is rarely or only sparingly used as a substrate for AD and thus the focus of straw utilization in energy production has focused on combustion that has inherent inefficiencies. However, the digestion of straw has been contemplated as the theoretical biogas potential of straw is high, i.e. $>400$ m$^3$ CH$_4$/tonne of volatile solids (VS). Mechanisms to convert the inherent organic carbon in straw in bio-available forms such as plasma treatment (Heiske et al. 2013) or enzymatic treatment (Komastu et al., 2007) have been examined at laboratory scale. At full deployment scale methods such as briquetting have been demonstrated by Moller & Hansen (2014). However, even this latter system operates at a relatively small scale, i.e. $<1,500$ tonnes per annum and where only 60% of the available CH$_4$ is being extracted using this method, i.e. $<0.5$ MWth.

A number of publications describe the treatment of energy crops and vegetable waste by so-called "steam explosion" in order to make cellular contents accessible. For example, US 2013/206345 (Dauser) explains that steam explosion is a technical process by which input material is heated up to 300° C., preferably to 150-200° C. at 3-20 bar for a period of time, after which the pressure is abruptly returned to atmospheric pressure. This rapid decompression is said to facilitate complete breakdown of cells, after which the cell contents are available in liquefied form for further processing. The Dauser specification describes a pressure vessel with an external heating jacket that is fed with input material in the form of short fibres or crumbs of particle size less than 5 cm that can comprise 30-90% dry straw which is pre-treated with steam within a bespoke heated screw conveyor. The material to be processed is introduced into a hydrolyser where it is agitated in an atmosphere of superheated steam at up to 180° C., the hydrolyser operating quasi-continuously, after which the material is fed to a depressurization unit including a cyclone where superheated steam is separated and a flash tank. Although the substrate being fed into the hydrolyser is treated with a defined volume of process water and is held in the hydrolyser for about 30 minutes before it passes to the depressurization unit, heating of the hydrolyser is by an external heating jacket fed with steam or heat from an oil or gas boiler. By definition superheated steam is free of liquid water, so that the added process water is boiled off in its entirety in the hydrolyser. However, superheated steam is a poor conductor of heat and once the process water in the input material which is added in small batches has volatilised, heat transfer between the wall of the hydrolyser and its contents becomes inefficient. Because heating is through the wall of the hydrolyser, the highest temperature is at its internal surface and formation of an aqueous layer on its internal surface is precluded. The process conditions therefore favour build-up of adhered material on the wall of the hydrolyser which will interfere with thermal hydrolysis and require process interruption and relatively frequent cleaning. Furthermore the initial pre-treatment of substrates described in Dauser (including straw as a possible component) is not optimised to maximise throughput where straw is the primary component. Specifically, the pre-treatment simply involves loading a hopper with substrate and moistening it with steam followed by initial processing within a heated auger apparatus ahead of the hydrolyser. In this regard, while the auger arrangement will allow for some compaction of the straw the system is unlikely to allow large inclusions of straw in the mix being fed to the hydrolyser as the bulk density will remain relatively low. This will impede the deployment of such systems for the conversion of straw at scale or the units required will be very large and inefficient in such applications or plurality of units will be required thus leading to further inefficiencies.

SUMMARY OF THE INVENTION

We have found that low density lignocellulosic material can be treated to allow the effective processing of the large volumes required to allow inclusion within AD systems at scale while making the organic content bio-available to microbial degradation. This involves the specific destruction of buoyancy while making the cell contents available for anaerobic digestion by treatment in a pressure vessel with saturated steam and without steam explosion. In an embodiment, therefore, the invention provides a method for preparing a fibrous primary lignocellulose biomass for anaerobic digestion, which comprises initially converting the low density voluminous material, e.g. straw, into a dense mass to optimise the mass loading within the subsequent pressure vessel to allow deployment at scale without having to rely on over-sized inefficient units or plurality of vessels. Larger installations (>5 $MW_{th}$) can however include for a plurality of this invention. In this invention the biomass is circulated in a pressure vessel through an atmosphere of saturated steam providing heat for thermal pressure hydrolysis and recovery of treated biomass from the vessel.

In an embodiment the invention provides a process of preparing a fibrous primary lignocellulose biomass for anaerobic digestion, which comprises:
  providing the biomass in a finely divided state;
  compressing the biomass and adding water, organic slurry or other aqueous liquid to said biomass to form a feed batch having a bulk density of ≥350 kg/m³ with a high proportion of lignocellulose dry matter content, e.g. >125 kg/m³ of moisture adjusted substrate loaded into the vessel.
  introducing the feed batch into a pressure vessel;
  introducing an atmosphere of saturated steam into the pressure vessel and maintaining said atmosphere at 133-220° C. and 2-10 bar whilst circulating the material of the feed batch through the saturated steam atmosphere for a time effective to induce internal collapse of the lignocellulose biomass cell structure;
  gradually depressurising the pressure vessel and cooling its contents; and
  recovering the hydrolysed lignocellulose biomass from the pressure vessel as an aqueous slurry in a sterilised state, with a disrupted cellular structure as a result of thermal pressure hydrolysis and with loss of its inherent buoyancy in aqueous liquids. The primary biomass may be straw, e.g. from barley, oats, rape, rice, rye, wheat or a mixture thereof and may at least partly comprises animal bedding material containing straw and other lignocellulose elements. Straw may be chopped to a convenient size where it will not aggregate into fibrous masses during subsequent anaerobic digestion and the biomass may comprises particle of maximum dimension <5 to 50 mm.

The feedstock may further comprises a secondary biomass which comprises animal manure e.g. of density ≥500 kg/m³, e.g. bovine slurry, pig slurry, chicken litter or a mixture of at least two of them.

Following thermal pressure hydrolysis using saturated steam, the recovered output will be low in anaerobic digestion inhibitory volatile fatty acid (VFAs) and ammonia compared with untreated substrates and will be reduced in animal and plant pathogens by >99.9% compared with untreated substrates.

The aqueous liquid added to the biomass may comprise water, organic slurry, wastewater, anaerobic digestion centrate or a mixture of them.

In embodiments, the pressure vessel has inlet and discharge ends and has a downward incline towards its discharge end. It may be rotary and may be provided with helical internal flights for circulating the material of the feed batch through the saturated steam atmosphere. Alternatively it may be non-rotary, inclined and may be internally stirred with rotary blades or paddles for circulating the material of the feed batch through the saturated steam atmosphere.

The pressure vessel may be evacuated between introduction of the feed batch and introduction of saturated steam, after which the steam may be introduced from a steam accumulator. The sole source of heat for the pressure vessel and its contents may be saturated steam which is supplied to bring the vessel and its contents to the temperature required for thermal pressure hydrolysis, and may continue to be supplied from the steam accumulator to maintain a working temperature and pressure. Thermal pressure hydrolysis may be at >5 bar and at >133-220° C. e.g. about 160° C./6 bar. Steam from completion of one cycle of material circulation may be used to heat the liquid used to mix with the lignocellulose input (slurry, centrate, water etc) in a buffer tank for the next cycle, or a pair of pressure vessels may be provided, steam from one TPH vessel in which material circulation has been completed being supplied to the other TPH vessel in which material circulation is about to begin. After the hydrolysis step the output is cooled and may be combined with digestate liquor, water and/or wastewater in a mixing tank which in embodiments may have an associated heat exchange for cooling the contents of the tank to a desired temperature ahead of transfer to the AD CSR.

The recovered digestate may be subjected to anaerobic digestion e.g. wet mesophilic or thermophilic anaerobic digestion, and biogas e.g. methane may be recovered.

In an embodiment the invention provides a feedstock for anaerobic digestion comprising a fibrous primary lignocellulose biomass in a finely divided state, a secondary biomass providing anaerobically digestible nitrogen and aqueous liquid, the primary biomass having a disrupted cellular structure such that its inherent buoyancy in aqueous liquid is lost and digestible carbon is released and the mixture being in the form of an aqueous slurry in a sterilized state.

The primary lignocellulose biomass of the feedstock may be straw e.g. from barley, oats, rape, rice, rye and wheat or a mixture thereof and the secondary biomass comprises animal manure e.g. bovine slurry, pig slurry, chicken litter or a mixture of at least two of them. The biomass may have a disrupted cellular structure as a result of thermal pressure hydrolysis and following TPH it will be low in releasable anaerobic digestion inhibitory volatile fatty acid and ammonia and will be reduced in animal and plant pathogens by >99.9% compared with untreated substrates.

BRIEF DESCRIPTION OF THE DRAWINGS

How the invention may be put into effect will now be described, by way of example only, with reference to the accompanying drawings, in which.

DETAILED DESCRIPTION OF PREFERRED EMBODIMENTS

As is well known, plants form two types of cell wall that differ in function and composition. Primary walls surround growing and dividing plant cells, provide mechanical strength but must also expand to allow the cell to grow and divide. A much thicker and stronger secondary wall accounts for most of the carbohydrate in biomass and is deposited once the cell has ceased to grow. The secondary walls of woody tissue and grasses are composed predominantly of cellulose, lignin, and hemicellulose (xylan, glucuronoxylan, arabinoxylan, or glucomannan). Cellulose fibrils are embedded in a network of hemicellulose and lignin. Cross-linking of this network results in the elimination of water from the wall is a major contributor to the structural characteristics of secondary walls but forms a waxy hydrophobic composite that limits accessibility to enzymes including those involved in biodegradation including anaerobic microbial digestion.

Thermal pressure hydrolysis using saturated steam can bring about cellular disruption which can facilitate subsequent anaerobic digestion and in the case of a naturally buoyant low-density material such as straw can cause the material to disrupted at a cellular level and become non-buoyant and hence compatible with subsequent anaerobic digestion in a digester in which a body of aqueous liquid in which digestion is taking place is contained in a stirred tank (CSR) under typical mesophlylic or thermophylic conditions. In brief anaerobic digestion includes three steps: (1) cellular disruption (hydrolysis), (2) conversion of carbonaceous macromolecules such as carbohydrates, lipids and proteins into acetate (acetogenesis) and (3) conversion of acetate to methane (methanogenesis). When a digester is fed with biomass that has been previously prepared and hydrolysed with saturated steam as described above, steps 2 & 3 are substantially accelerated as hydrolysis is the rate limiting step. Moreover, as saturated steam hydrolysis is substantially more effective for lignocellulose materials than typical microbial hydrolysis at mesophilic temperatures with low pressure pre-treatment regimes, the yields of bio-available carbon in step 2 is optimised. Therefore more biogas will be produced in step 3 for saturated steam hydrolysed lignocellulose materials than non-hydrolysed materials at the same loading rates. That means that firstly very high inclusions of lignocellulose materials can be used in digestion and secondly, shorter retention time can be used on the hydrolysed material and digester volume can be reduced or throughput increased for a given digester volume.

Lignocellulose substrates that are targeted for use in the present process primarily include straw (e.g. from barley, wheat, oats, rape, rice) as a by-product of food crop production but can also include other low density lignocellulose biomass such as miscanthus, reeds, crop residuals and green cuttings. An embodiment of the process is also aimed at the optimum co-digestion of lignocellulose animal bedding and fibrous manure. This process can also use secondary straw, i.e. straw that has been used for animal bedding wherein a large proportion of the methane potential of the material remains thus facilitating its primary use in a very sustainable manner. Similarly, spoiled straw that has become too wet for combustion or bedding can be processed. Overall it is envisaged that the process may in some embodiments be scaled to process between 10,000-20,000+ tonnes per annum within a single optimized vessel as per this invention with larger facilities operating with a plurality of such systems. Smaller systems are also possible. This approach also means that 100% of the straw generated in the UK or elsewhere would be available for digestion, i.e. straight from the fields or after being used as bedding or deemed spoiled for other uses such as combustion or as manure after use as a feed component. This is a considerable advantage from the standpoint of scope of supply compared with combustion where only field dry straw can be utilized at large scale typically >100,000 tonnes per annum).

This combined system of pre-treating and anaerobically digesting lignocellulose biomass such as straw results in a methane productivity that is actually superior to conventional feedstocks. Specifically, as straw has an inherently high DS (dry solids) and VS (volatile solids) content and once rendered bio-available via this invention, straw may be substantially more productive compared with conventional agricultural inputs to AD such as silage. Specifically one tonne of straw with a DS of 85% and a volatile solids (VS) content of 95% represents approximately 800 kg of available carbonaceous material per tonne of biomass once subject to pre-treatment with this invention. This contrasts with the benchmark material for biogas production i.e., maize silage, where one tonne will only yields <350 kg of available carbonaceous DS per tonne of biomass presented due to the higher inherent moisture content of typical silage. Therefore even though maize silage typically has a superior unit biomethane productivity (circa. 378 m$^3$ CH$_4$/t VS) compared with straw processed as described in this invention (circa. 350 m$^3$ CH$_4$/t VS), the unit production per tonne of fresh material delivered to the AD facility is substantially superior in the case of straw, i.e. circa. 282 m$^3$ CH$_4$/t of fresh straw material compared with circa. 125 m$^3$ CH$_4$/t of fresh maize silage due to the inherent moisture content. This difference of circa. 225% thus renders an AD plant utilizing lignocellulose agricultural residual inputs substantially more efficient than plants processing energy crops that directly displace food production from scare productive agricultural land resources. Furthermore, as straw is a by-product of food production it is substantially more sustainable than purposely grown energy crops such as maize that displace productive arable land from food production.

Figure 2:
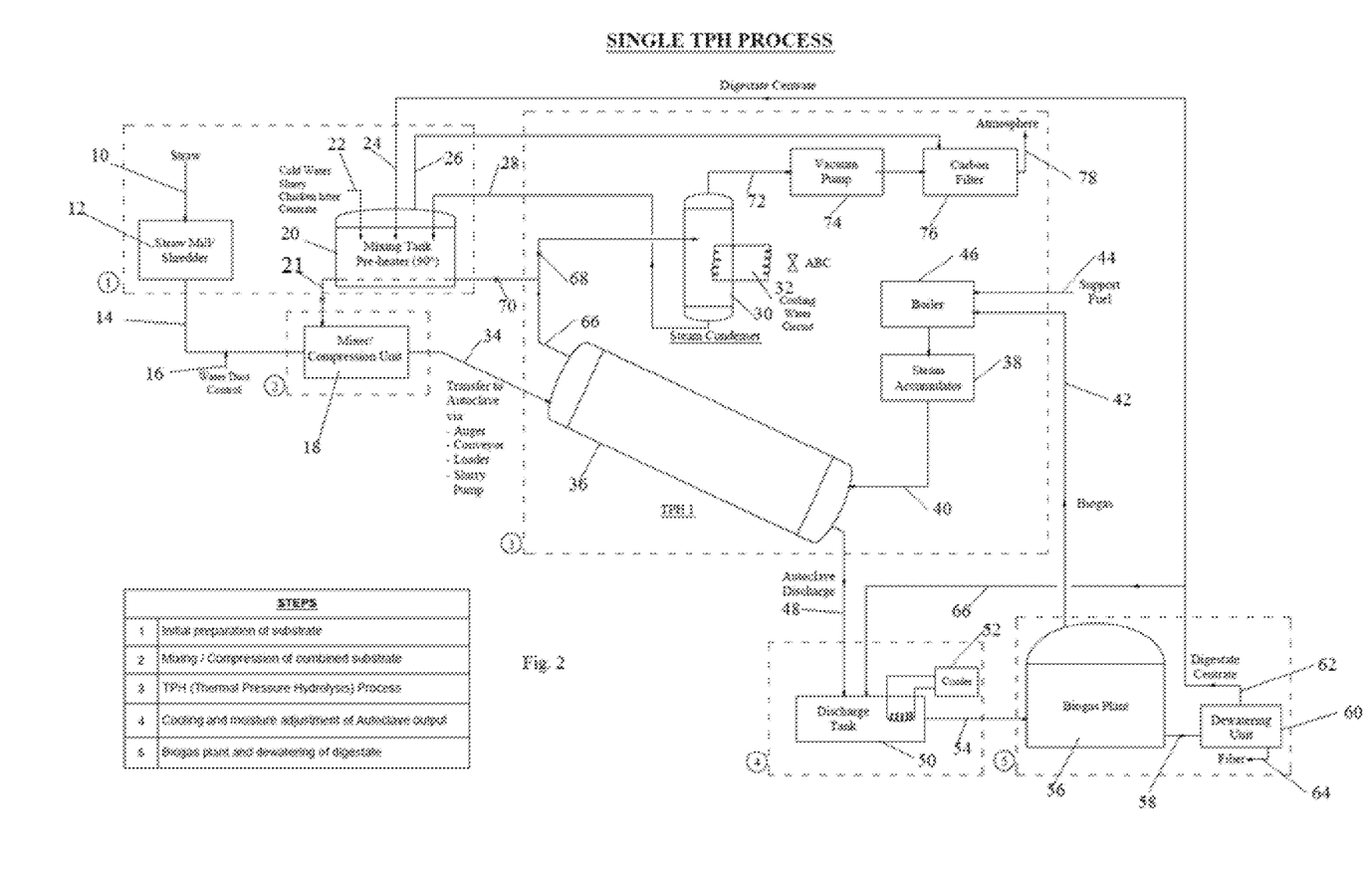
FIG. 2 shows diagrammatically a first embodiment of a plant for treating lignocellulose biomass.
Figure 4:
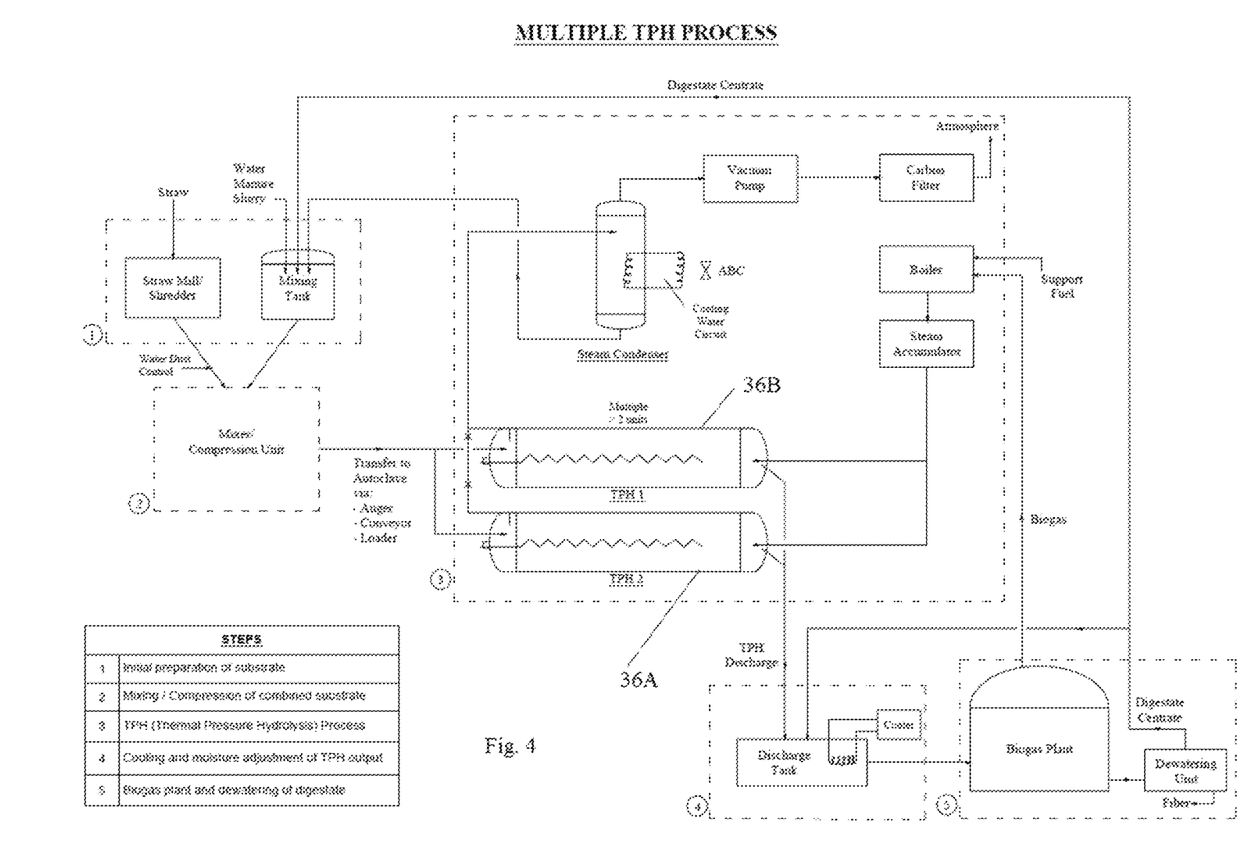
FIG. 4 shows diagrammatically a second embodiment of a plant for treating lignocellulose biomass.

As seen in FIGS. 2 and 4, a first step of the present process is the preparation of substrates to ensure optimum straw loading per batch, i.e. >125 kg of straw DS per m$^3$ of infeed. Straw supplied at 10 passes to a straw mill or shredder 12 where it is shredded and/or reduced in length. Apparatus for performing this task is commercially available. For example, the Roto Grind 760 tub grinder machines using rotating and static blades to chop straw to a constituent short length e.g. about 50 mm and with extra blades to 30-35 mm and can accept bales of straw up to 1.5 m in diameter and similar equipment is available from other manufacturers. Shredding may be down to 20 mm e.g. as short as 10 mm, and an industrial straw shredder said to incorporate a chopping system capable of reducing straw to 10 mm in length is available from Larrington Trailers of Boston, UK, an in-line tube shredder also being available from that company, see e.g. EP-A-0860108 (Lucas), GB-A-2477076 (Larrington) and WO 2014/091240 (Larrington). Shredded straw in line or conveyor 14 is treated with water or other aqueous liquid at line 16 inter alia for dust control.

Manure e.g. slurry and chicken litter are supplied to a mixing tank 20 where they are mixed with centrate/digestate liquor from anaerobic digestion at line 24 and optionally with water, the contents of the tank being pre-heated to 60-75° C. with steam from pressure tank 35 via lines 66 and 70 and/or from steam condenser 30 via line 28. As tank 20 becomes filled, air within it can be vented via line 26 and carbon filter 76 and discharged to atmosphere.

The straw from line 14 and slurry passing in line 21 from mixing tank 20 passes to a mixer/compression unit 18. Importantly, this horizontal auger mixer, with counter rotating augers e.g. an Italmix Matrix Argon compost mixer compress the shredded straw and added liquids together to create a mass with a relatively high bulk density compared with straw that is simply moistened and mixed using conventional paddle mixers. In this regard the straw and slurry are combined and compressed to give a combined feedstock of density of e.g. 300-600 kg/m$^3$ and a carbon to nitrogen (C:N) ratio which may be 20-60 i.e. a C:N ratio of between 25-40 is ideal for mesophilic anaerobic digestion at about 35° C. Transfer of the combined and densified feedstock is transferred to pressure vessel 36 by any suitable means e.g. a slurry pump, loader, conveyor or auger.

The next step is thermal pressure hydrolysis by tumbling the feedstock in an atmosphere of wet steam in pressure vessel 36 at >5 bar and at >133-220° C. e.g. about 160° C. and about 6 bar. The pressure vessel 36 which may be downwardly inclined e.g. at about 15° may have an insulating jacket to reduce unwanted heat loss, but is heated solely internally and solely by wet steam from steam accumulator 38 introduced into its lower end via line 40. Because the atmosphere is of wet steam, the interior surface of the pressure vessel is covered with a thin layer of liquid water, and unwanted adhesion of organic material is not promoted. The steam in accumulator 38 is generated using boiler 36 fed with biogas in line 42 from anaerobic digestion and if necessary also with auxillary fuel in line 44, the saturated steam in accumulator 38 being maintained e.g. at about 20 bar. In the FIG. 2 embodiment the pressure vessel may be rotary and may be provided with internal flights for circulating the feedstock. Treatment times will depend on the temperature employed but in some embodiments may be 20-90 minutes.

On completion of treatment, the saturated steam in the pressure vessel 36 may be condensed by addition of sufficient cold water to reduce the internal temperature below 100° C. In addition or as an alternative the atmosphere is vented e.g. through line 66 from the upper end of the pressure vessel, opposite to where steam is introduced. Steam in line 66 may be passed to line 70 and used to pre-heat the contents of mixing tank 20; in addition or as an alternative it may be passed through line 68 to steam condenser 30 cooled by water cooling coil 32. After the filling stage of the hydrolysis cycle, the lines 66, 68 may also be used for evacuation of air in the vessel 36 by line 72 and vacuum pump 74, the air also passing through carbon filter 76 and thence to atmosphere at 78. hydrolysed biomass from the TPH vessel is discharged from its lower end at line 48 to discharge tank 50 where its moisture content may be adjusted and mixed. It may be cooled by cooler 52 that is thermostatically controlled to achieve precise temperature of the output ahead of transfer to anaerobic digestion where heat shock could potentially inhibit the subsequent digestion process.

The treated material then passes from discharge tank 50 via line 54 to the AD plant 56 where it undergoes mesophilic or thermophilic wet anaerobic digestion. Biogas passes from line 42 e.g. to boiler 46 and also may be recovered at an output line (not shown). Solids in slurry form passes from biogas plant 56 to dewatering unit 60 in which centrate liquid is recovered to line 62 and recycled and solids are removed at line 64.

Figure 3:
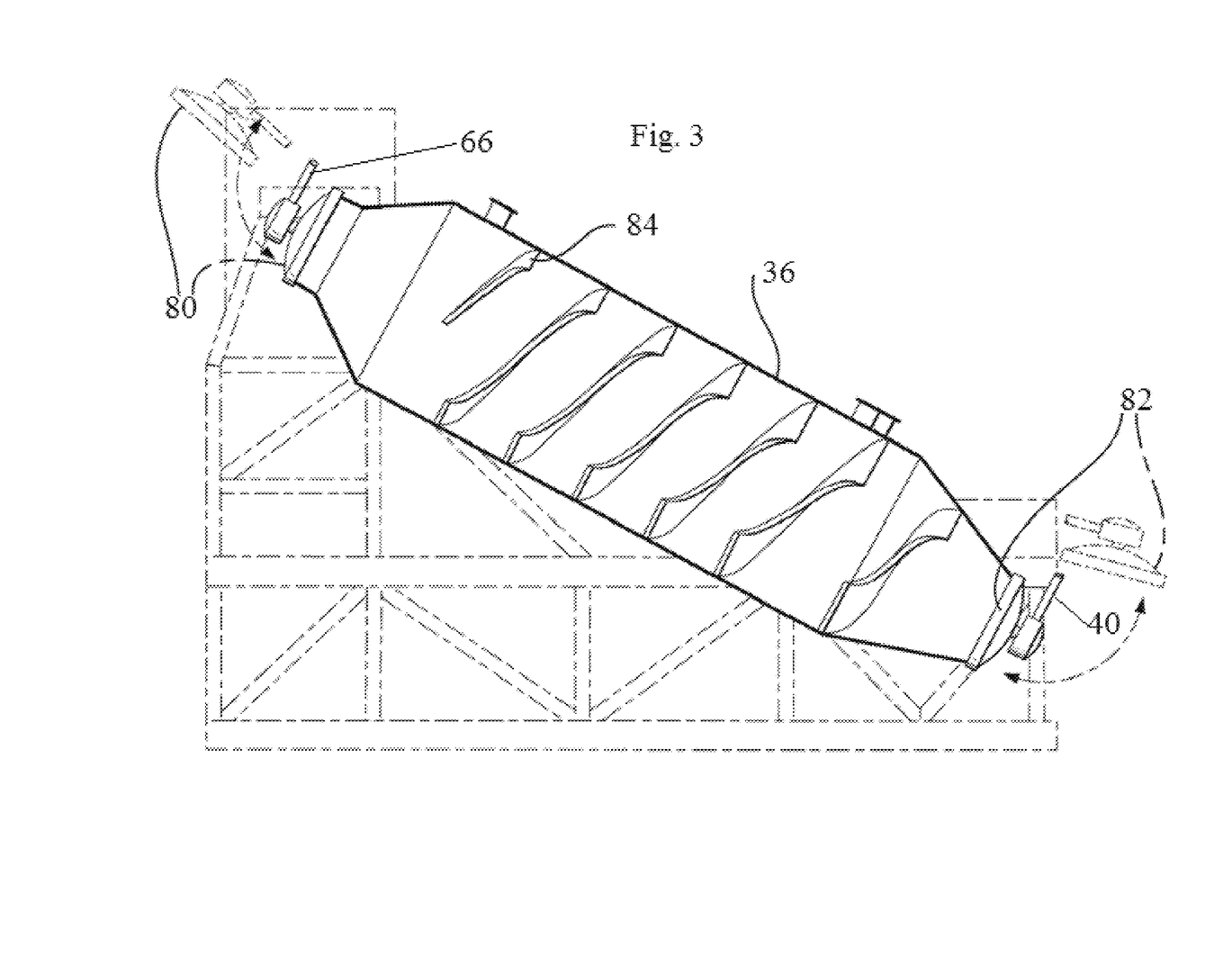
FIG. 3 is a view in longitudinal section of a rotary pressure vessel forming part of the treatment plant of FIG. 2.

A representative rotary pressure vessel is described in some detail in WO 2012/172329 (Toll) and is shown diagrammatically in FIG. 3 and is provided with inlet and discharge doors 80, 82 respectively connected to lines 40 and 66 and internal flights 84. If the pressure vessel is rotated in one direction the flights 84 in addition to circulating the feedstock forwards it towards the lower discharge end and when rotated in the other direction lifts the material from the lower end while maintaining circulation of the material. On completion of the vacuum pre-treatment stage which may last about 15 minutes, steam and optionally further water are introduced through door 82 to raise the internal temperature of the pressure vessel e.g. to about 160° and to about 6 bar. Pressurization of the TPH vessel may take some minutes, quantities of the introduced steam condensing in the initially relatively cold load to increase the water content thereof. Circulation of the load through the TPH vessel by reverse rotation may be carried out, and even load distribution may be monitored by transducers measuring weight at upper and lower ends of the rotary vessel to check that the load has not compacted and remains at the bottom of the vessel. Penetration of the steam into and through the load is gradual, and pressure is monitored at both ends of the TPH vessel, rise of pressure at the upper end of the TPH vessel to or close to the rated processing temperature ~160° C. indicating that the pressurization step is complete. By introducing steam from the lower end and monitoring pressure (or temperature) at the upper end of the vessel, it is possible to ensure that the whole of the load has been penetrated by the steam. Processing at the working temperature and pressure is then carried out for a period of time effective to break down the load and in particular the lignocellulosic content thereof.

The arrangement of FIG. 4 is similar to that of FIG. 3 except that there is in this case a pair of in this instance non-rotary internally stirred treatment vessels 36A and 36B. The treatment vessels may be used alternately with steam form one vessel at the end of one hydrolysis cycle being used to pre-heat the other vessel and its contents at the start of the next processing cycle.

How the invention may be put into effect will now be described, by way of illustration only, in the accompanying Examples.

Example 1

Barley straw and onlytap water were combined and processed as described above with reference to FIGS. 2 and 3 above, and then subjected to wet mesophilic anaerobic digestion.

Specifically, after mixing as described in this invention the composite material has loaded into a rotary TPH vessel as described with reference to and as illustrated in FIGS. 2 and 3 and operated at 6.2 bars abs/160° C. by the injection of steam and when the temperatures had equalised through the vessel the load was left to hydrolyse for 45 minutes while the TPH vessel continued to rotate. For the depressurisation stage at the end of that period the vessel was isolated from the steam supply and was connected to its dedicated spray condenser system which allowed the TPH vessel to be depressurised to below atmospheric pressure. Finally a vent valve was opened to allow air back into the vessel to bring it back to atmospheric pressure. The bottom TPH vessel door was then opened and the load discharged.

Six cylindrical CSRs, each of which has a working volume of 2.0 litres, were used for these trials. Each reactor was made of PVC pipe with a screwed gas-tight top with ports to allow feed additions, effluent removal, gas collection and which also supports a stirring motor. The stirrers themselves were of a picket fence design with a drive shaft inserted into the reactor through a sealed coupling and were each is driven by a 40 rpm DC motor. The digesters were maintained in a water bath temperature controlled at a constant level of 37° C. Biogas was collected by water displacement using a gas outlet tube connected to a 10 litre gas collector. The experiments were carried out in duplicate. Two inoculum control digesters were also run alongside fed with seed sludge and tap water only. The seed sludge was collected from a sewage work in Millbrook Southampton. The inoculums were prepared by screening (1 mm mesh) large inert and undigested substrates. The screened inoculums' pH values and solids contents were measured and recorded.

pH was measured using an Accumet AB15, pH meter. Dried solids (DS) and volatile solids (VS) were measured gravimetrically using a fan assisted oven (105° C.) and muffle furnace (550° C.) respectively according to standard methods. From these measurements the moisture content and ash concentration of the samples were also obtained. Biogas composition ($CH_4$ and $CO_2$) were determined using a Varian CP-3800 gas chromatograph.

The BMP experiment was carried out for 30 days. The ratio of inoculums volatile solids to substrate volatile solids was 4.1:1. After feeding was completed the digesters were put into the water bath and connected to the gas collectors. The biogas production and the gas compositions in terms of methane ($CH_4$) and carbon dioxide ($CO_2$) were monitored periodically. Room temperature and atmospheric pressure were also recorded in order to correct the gas volumes produced by each digester to the volume at standard temperature and pressure (STP: zero ° C. and one atmospheric pressure). Volumes of biogas generated by the substrates sample A and B were calculated by subtracting the gas volume generated by the control digester from that produced by the substrates digesters. The data for the TPH straw and water and the milled straw and water is illustrated in Table 2.

TABLE 2

| Items | TPH straw | Milled straw |
|---|---|---|
| Total Dry Solids DS % | 90.4 | 90.4 |
| Total Volatile Solids % | 94.7 | 94.7 |
| Total biogas produced (at STP), L | 10.16 | 9.32 |
| Biogas produced by substrate (at STP), L | 6.07 | 5.32 |
| Total methane produced (at STP), L | 6.36 | 5.42 |
| Methane produced by substrate (at STP), L | 3.89 | 2.95 |
| VS of substrate added, g | 10 | 10 |
| Specific biogas yield, $m^3$/kg VS added | 0.607 | 0.532 |
| Specific methane yield, $m^3$ $CH_4$/kg added | 0.389 | 0.295 |

Figure 5:
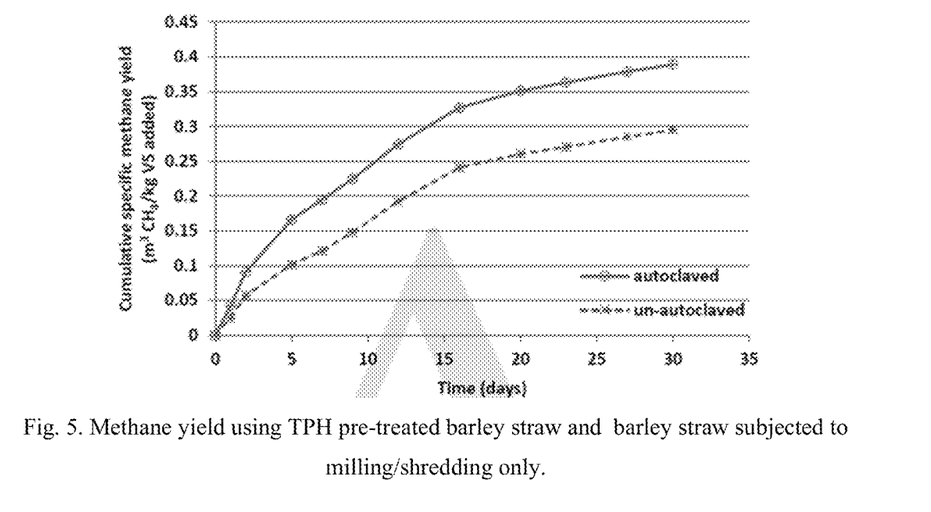
FIG. 5 is a graph showing methane yield using pre-treated barley straw and barley straw subjected to milling/shredding only.

Cumulative specific methane yield in $m^3$ $CH_4$/kg of volatile solids added was plotted as a function of time and the resulting graph forms FIG. 5 of this application. It will be noted that the TPH straw demonstrates an increase in specific methane yield of about 32% compared to milled straw. In practice this differential will be much higher as the level of straw inclusion within full scale anaerobic digesters will be limited due to the mechanical issues described.

Example 2

A variety of agricultural lignocellulose wastes were delivered for TPH trials. They included shredded barley straw, cattle slurry, chicken litter A which is from chickens purposely grown for egg production, and chicken litter B which is from chickens purposely grown for meat production. These residues have different mass densities and moisture contents. The analysis results are listed in Table 3.

TABLE 3

| Properties of the agricultural residues | | | |
|---|---|---|---|
| Materials | Density, kg/$m^3$ | DS, % | VS, % of DS |
| Barley straw | 32.5 | 90.4 | 94.7 |
| Chicken litter (egg laying) | 975 | 27.1 | 60.5 |
| Chicken litter (meat) | 500 | 32.7 | 76.8 |
| Cattle slurry | 1008 | 5.6 | 82.1 |

In a TPH trial the following agricultural residues were combined for processing. Additional moisture was also introduced into the TPH vessel. The mixing ratio is as shown below:

| | |
|---|---|
| cattle slurry | 45 kg |
| barley straw | 15 kg |
| chicken litter | 5 kg (2.5 kg each type) |
| water | 30 kg. |

After 45 minutes processing under the direct steam pressure of 6 bar (160° C.), 105 kg of hydrolyses output including condensate was produced. The hydrolyses output had a dry solids (DS) content of 17.3% of which 89% were volatile solids (VS).

Samples of processed and unprocessed composite substrates were then taken for biological methane potential (BMP) test. As previously explained, six 2 litre working volume digesters were used. Duplicated experiments were set up for each sample alongside a pair of digesters for seed inoculums control.

Figure 6:
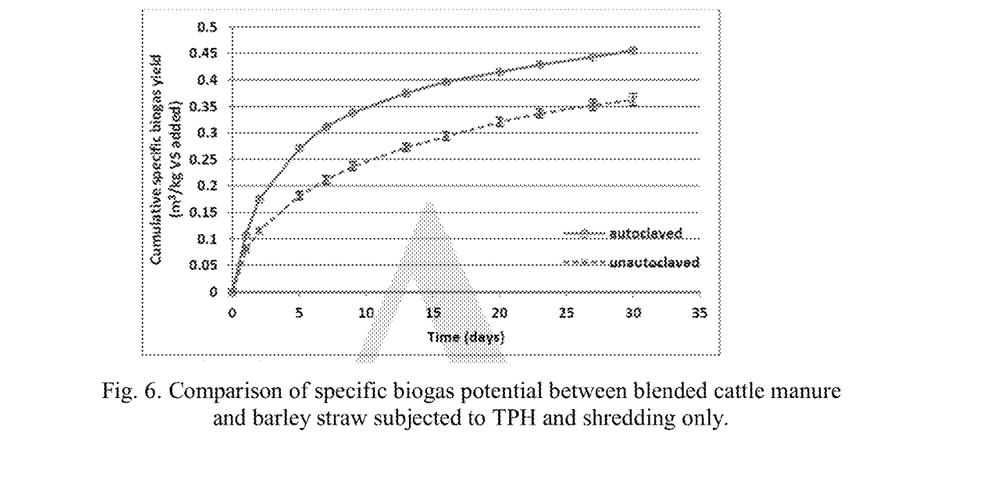
FIG. 6 is a graph showing a comparison of specific biogas potential between blended cattle manure and barley straw subjected to TPH and shredding only.
Figure 7:
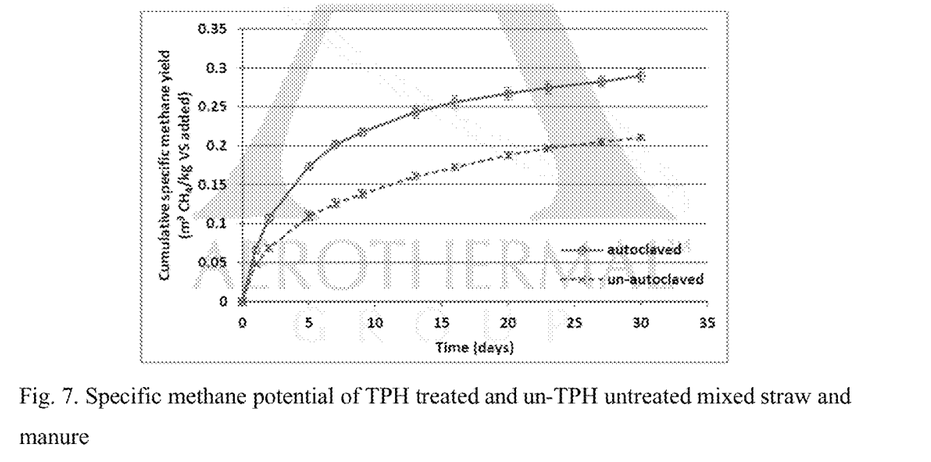
FIG. 7 is a graph showing specific methane potential of treated and un-treated mixed waste.
Figure 8:
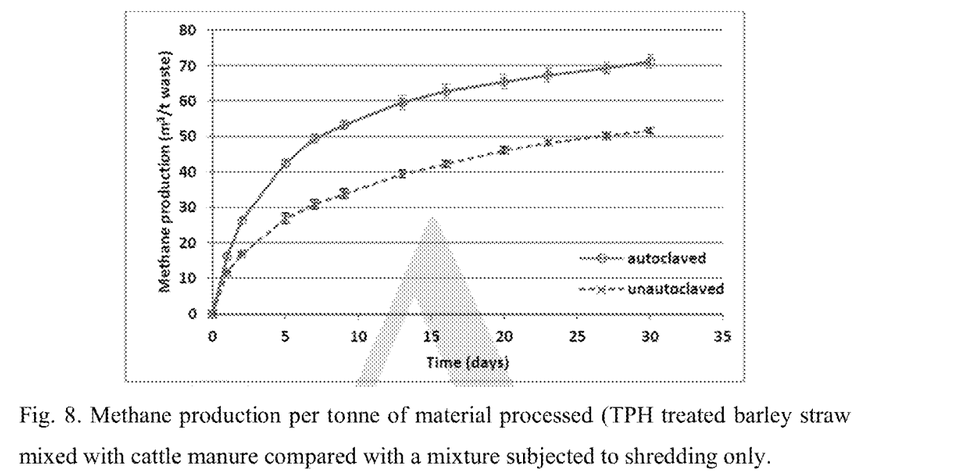
FIG. 8 is a graph showing methane production per tonne of material processed (TPH treated barley straw mixed with cattle manure compared with a mixture subjected to shredding only).

The specific biogas yields and specific methane production of the treated and control samples A and B are shown in FIGS. 6 & 7. FIG. 8 shows the potential methane production for processing one tonne of the composite substrate. Results are also summarised in Table 4.

TABLE 4

Summarised results of 30 day BMP test for straw and manure composite

| Items | TPH Straw & manure | Milled straw & manure |
|---|---|---|
| Total biogas produced (at STP), L | 9.81 | 8.88 |
| Biogas produced by substrate (at STP), L | 4.56 | 3.63 |
| Total methane produced (at STP), L | 6.06 | 5.27 |
| Methane produced by substrate (at STP), L | 2.91 | 2.11 |
| VS of substrate added, g | 10 | 10 |
| Specific biogas yield, m³/kg VS added | 0.456 | 0.363 |
| Specific methane yield, m³ CH$_4$/kg added | 0.291 | 0.211 |

The above results demonstrate that processing one tonne of straw mixed with manure using the above process could potentially produce about 71 m³ of bio-methane, which is 37% more than the unprocessed control.

The invention claimed is:

1. A process of preparing a fibrous primary lignocellulose biomass for anaerobic digestion, which comprises:
   providing the fibrous primary lignocellulose biomass in a finely divided state;
   compressing the biomass and adding water and/or organic slurry to the biomass to form a feed batch having a bulk density of >350 kg/m³;
   introducing the feed batch into a pressure vessel wherein the feed batch contains >125 kg of the biomass per m³ and wherein the pressure vessel is rotary, has inlet and discharge ends provided with inlet and discharge doors and has a downward incline towards its discharge end;
   introducing an atmosphere of saturated steam into the pressure vessel and maintaining the saturated steam atmosphere within the pressure vessel at 133-220° C. and 3-10 bar for thermal pressure hydrolysis whilst circulating the biomass through the saturated steam atmosphere within the pressure vessel by helical internal flights of the pressure vessel for a time effective to induce internal collapse of the lignocellulose;
   gradually depressurizing the pressure vessel to atmospheric pressure or lower and cooling its contents; and
   recovering a hydrolyzed lignocellulose biomass from the discharge end of the pressure vessel as a slurry or sludge in a sterilized state, with a disrupted cellular structure as a result of the thermal pressure hydrolysis and with loss of an inherent buoyancy of the biomass in aqueous liquids.

2. The process of claim 1, wherein the primary lignocellulose biomass comprises straw.

3. The process of claim 2, wherein the straw has any of the following features:
   (a) it is from barley, oats, rape, rice, rye and wheat or a mixture thereof;
   (b) it comprises particles of size <5 to 50 mm;
   (c) it comprises animal bedding material containing straw.

4. The process of claim 2, wherein the feed batch further comprises a secondary biomass which comprises animal manure.

5. The process of claim 4, wherein the animal manure
   (a) is of density >500 kg/m³; and/or
   (b) comprises bovine slurry, pig slurry, chicken litter or a mixture of at least two thereof.

6. The process of claim 4, wherein the hydrolyzed lignocellulose biomass recovered from the discharge end of the pressure vessel
   (a) is low in anaerobic digestion inhibitory volatile fatty acid and ammonia; and/or
   (b) is reduced in animal and plant pathogens by >99.9%.

7. The process of claim 2 having any of the following features:
   (a) the pressure vessel is evacuated between introduction of the feed batch and introduction of saturated steam;
   (b) the steam is introduced from a steam accumulator;
   (c) the thermal pressure hydrolysis is at 5-10 bar and at 133-160° C.;
   (d) the thermal pressure hydrolysis is at about 160° C.;
   (e) steam from completion of a cycle of biomass circulation is used to heat the organic slurry to be combined with the straw for the next cycle.

8. The process of claim 1, wherein a pair or plurality of pressure vessels is provided, and steam from one pressure vessel in which biomass circulation has been completed being supplied to the other pressure vessel in which biomass circulation is about to begin.

9. The process of claim 1, further comprising adjusting the hydrolyzed lignocellulose biomass recovered from the thermal pressure hydrolysis by combining with a liquor from an anaerobic digestion, water and/or wastewater in a mixing tank.

10. The process of claim 9, wherein a heat exchanger associated with the mixing tank cools and controls the temperature of the contents thereof to meet the requirements of a subsequent anaerobic digestion phase.

11. The process of claim 10, further comprising subjecting the recovered hydrolyzed lignocellulose biomass to anaerobic digestion.

12. The process of claim 11, comprising subjecting the recovered hydrolyzed lignocellulose biomass to wet mesophilic or thermophilic anaerobic digestion.

13. The process of claim 11, further comprising recovering methane from the anaerobic digestion.

\* \* \* \* \*